United States Patent [19]

Hines et al.

[11] Patent Number: 5,378,915
[45] Date of Patent: Jan. 3, 1995

[54] APPARATUS AND METHOD FOR AUTOMATIC TRACKING OF A ZOOMED SCAN AREA IN A MEDICAL CAMERA SYSTEM

[75] Inventors: Horace H. Hines, San Jose; Brian J. Walsh, Danville; Ronald Koops, San Leandro; Steven M. Jones, Pleasanton, all of Calif.

[73] Assignee: ADAC Laboratories, Milpitas, Calif.

[21] Appl. No.: 219,645

[22] Filed: Mar. 28, 1994

Related U.S. Application Data

[62] Division of Ser. No. 981,367, Nov. 25, 1992, Pat. No. 5,304,806.

[51] Int. Cl.$^6$ .......................... G01T 1/17; G01T 1/166
[52] U.S. Cl. .......................... 250/369; 250/363.04
[58] Field of Search .......................... 250/363.04, 369

[56] References Cited

U.S. PATENT DOCUMENTS 3,983,394  9/1976  Martone et al. ............... 250/363.02
4,503,331  3/1985  Kovacs, Jr. et al. ........... 250/363.04

FOREIGN PATENT DOCUMENTS 61-160078   7/1986  Japan ............................. 250/369
62-49281    3/1987  Japan ............................. 250/363.04
2250670    10/1992  United Kingdom ............ 250/363.04

Primary Examiner—Constantine Hannaher
Attorney, Agent, or Firm—Blakely, Sokoloff, Taylor & Zafman

[57] ABSTRACT

A system for automatically positioning zoom regions located on imaging surfaces of an ECT camera system during ECT rotation to track relative movement of an object that is located offset from the center of rotation of the ECT camera system. During an ECT scan session, the imaging surfaces of the camera system rotation about an object of interest that is located offset from the center of rotation of the camera system in order to minimize the separation between the imaging surfaces and the object surface. Since the object of interest is offset from the center of rotation, a predetermined zoom region located on the imaging surfaces must alter its position relative to the imaging surface during an ECT scan session in order to remain aligned with the object being imaged. The system determines this alignment position and thereby adjusts, in real-time, the location on the imaging surface of the zoom regions for increased image quality.

29 Claims, 4 Drawing Sheets

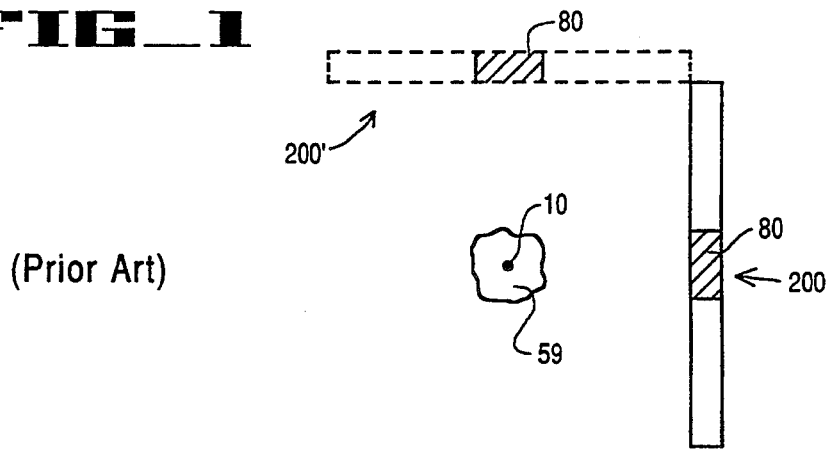
FIG_1 (Prior Art)
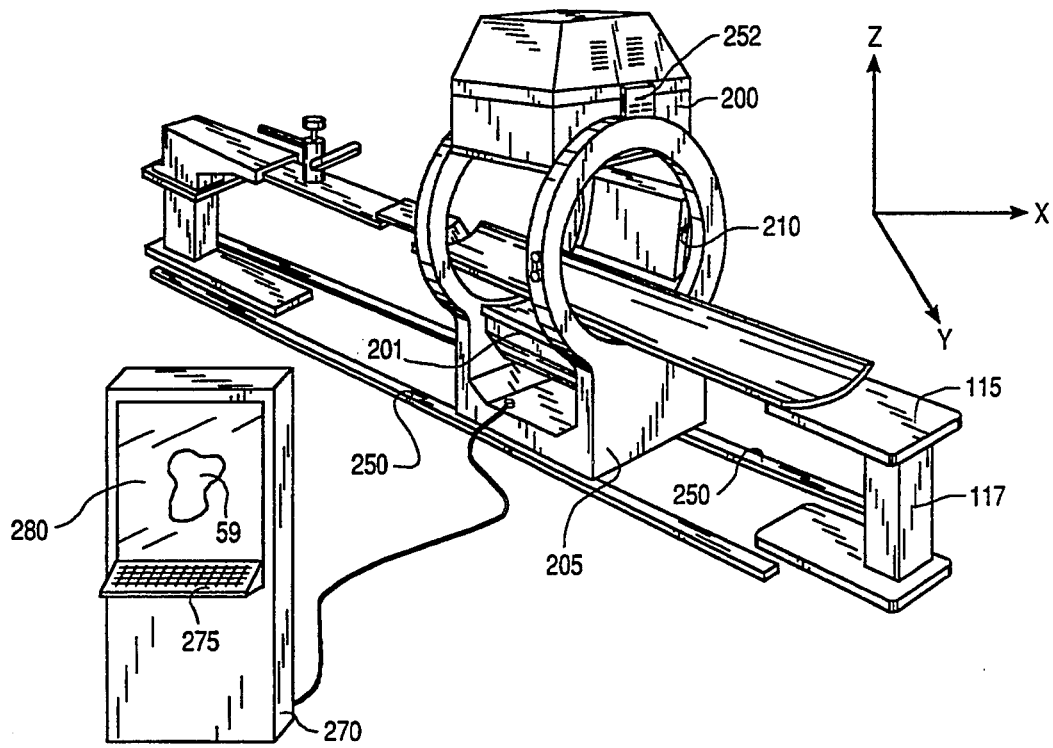
FIG_2
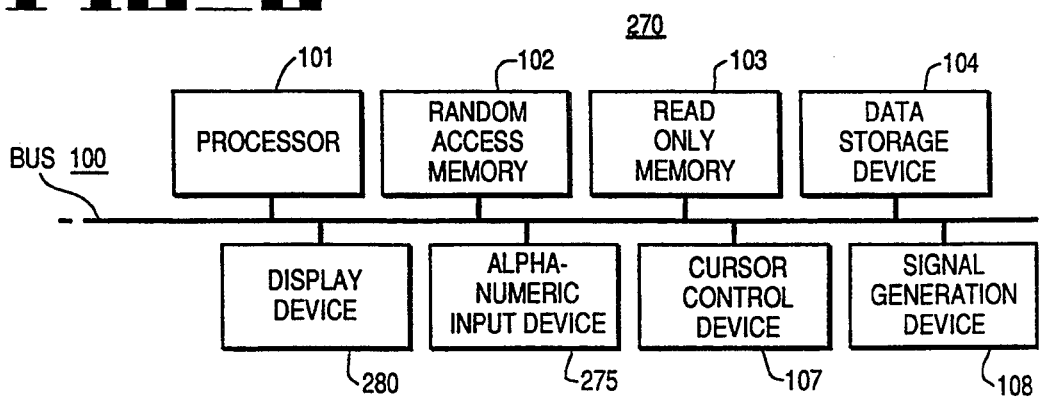
FIG_3

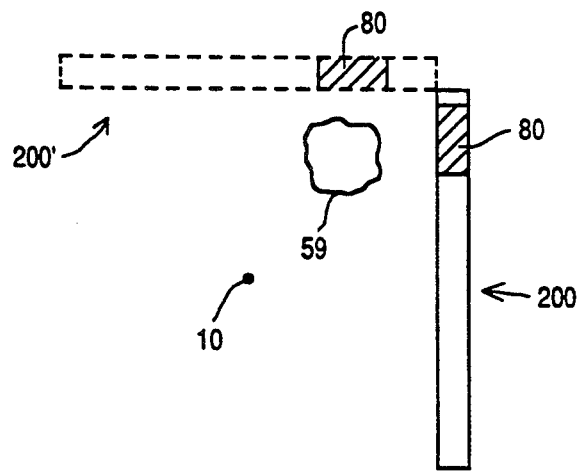
FIG_4
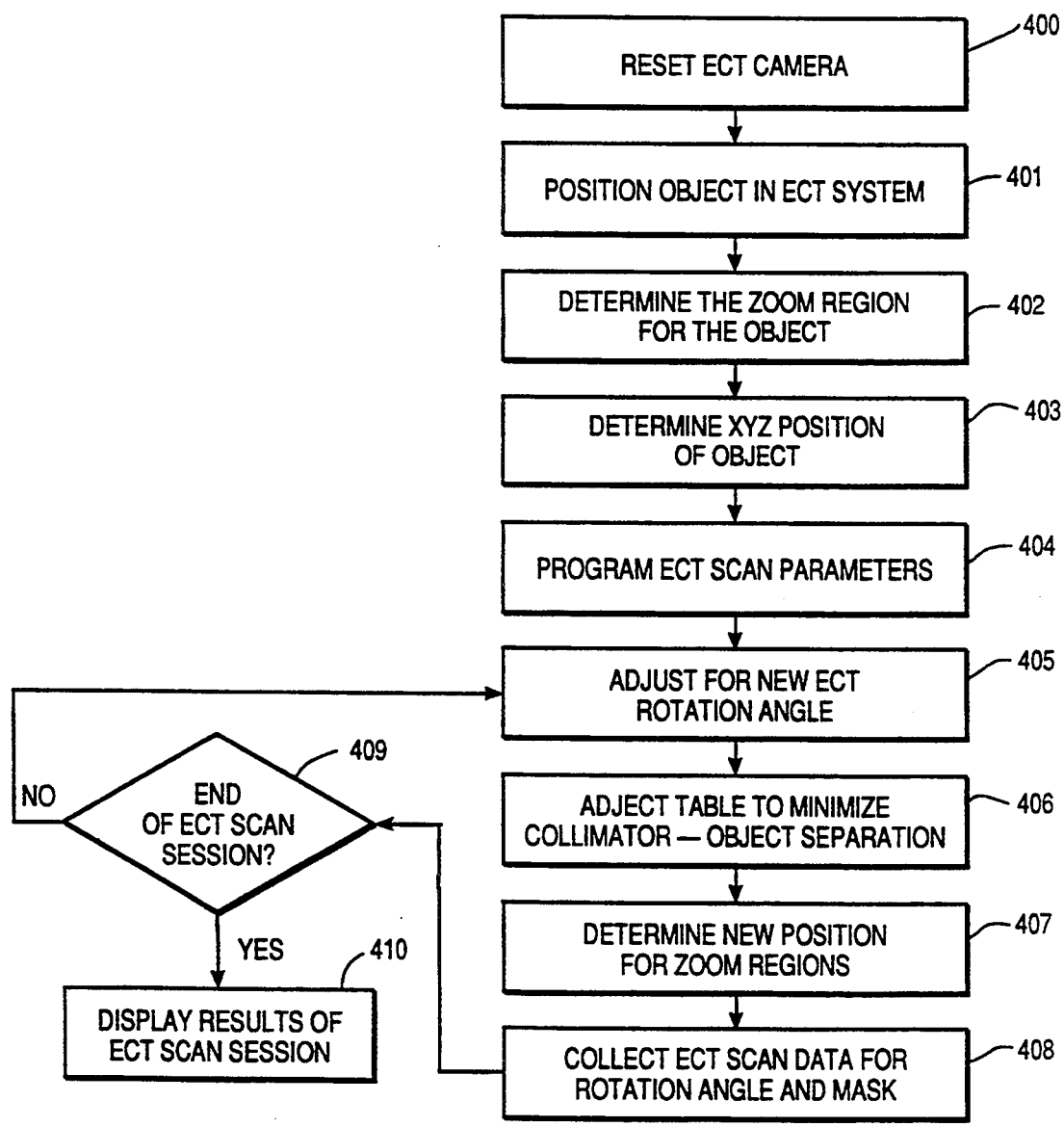
FIG_5

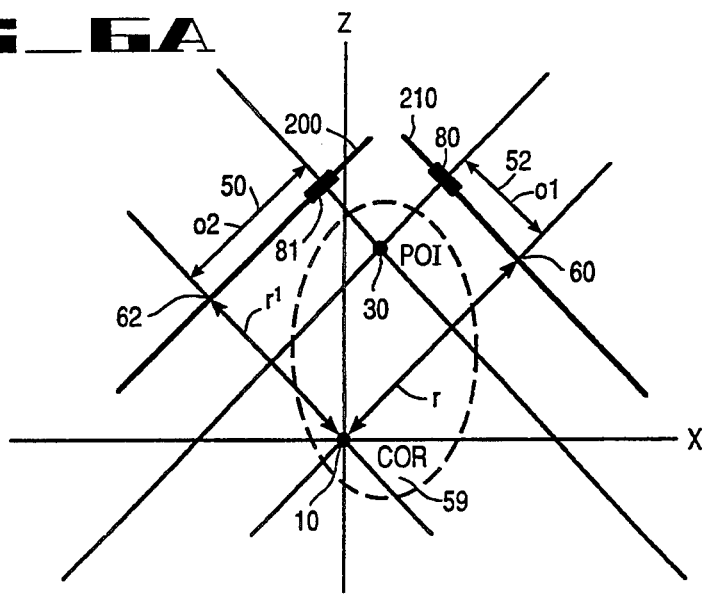
FIG_6A
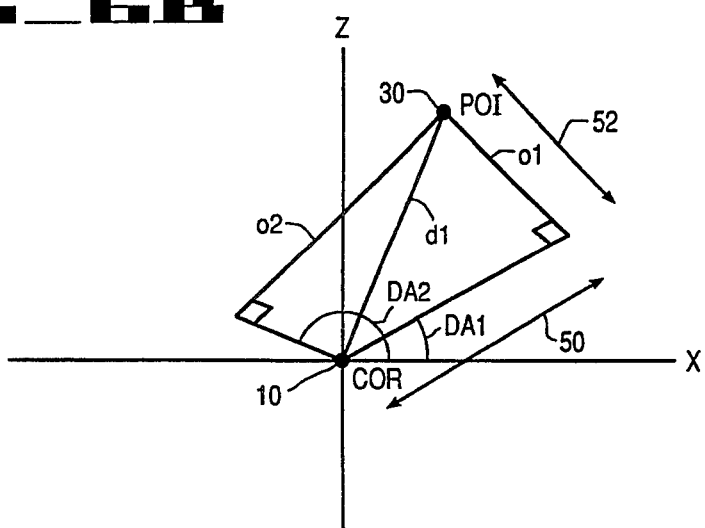
FIG_6B
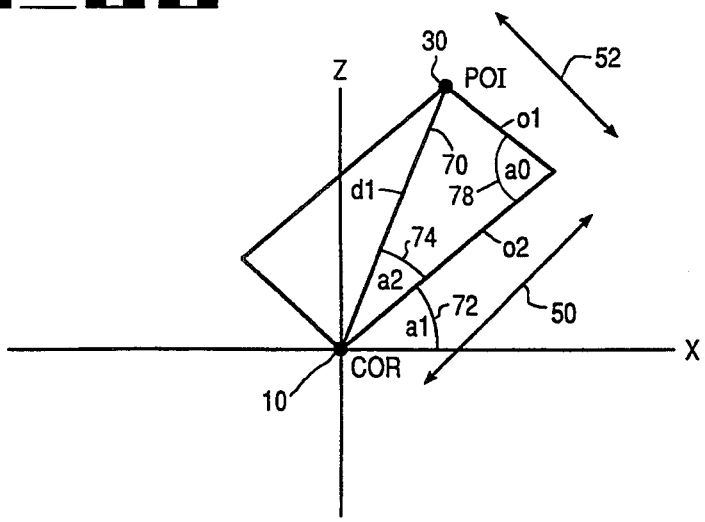
FIG_6C

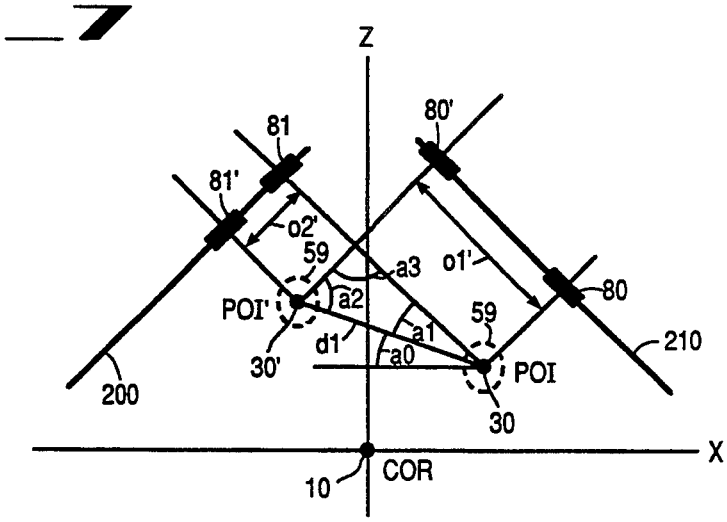
FIG_7
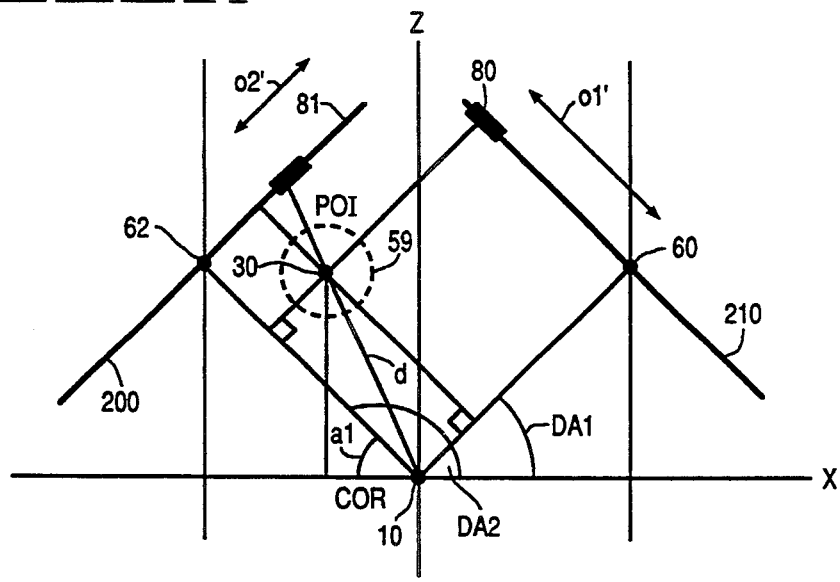
FIG_8A
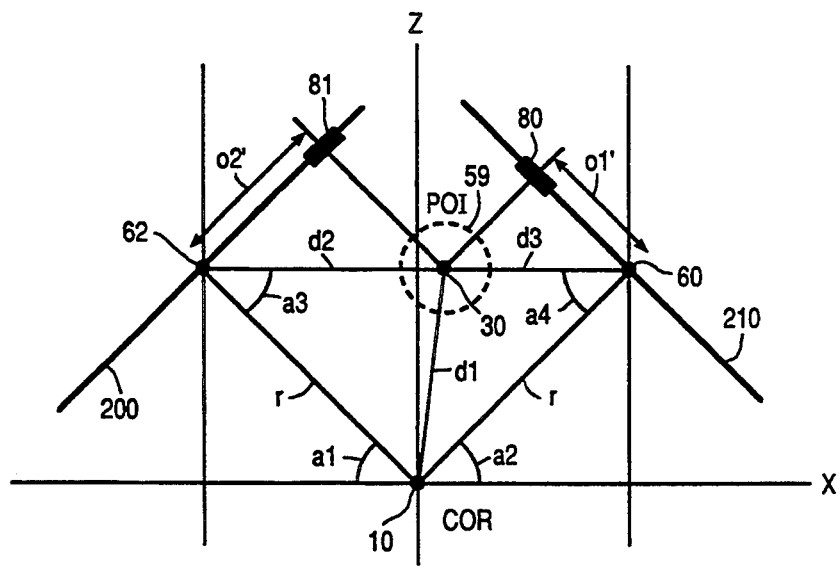
FIG_8B

APPARATUS AND METHOD FOR AUTOMATIC TRACKING OF A ZOOMED SCAN AREA IN A MEDICAL CAMERA SYSTEM

This is a continuation of application Ser. No. 07/981,367, filed Nov. 25, 1992, now U.S. Pat. No. 5,304,806.

BACKGROUND OF THE INVENTION

1. Field of the Invention

The present invention relates to the field of zoom techniques for imaging. Specifically the present invention relates to the field of tracking an object with a varying position of a zoom area in an ECT nuclear medicine imaging camera system providing a varying field of view.

2. Prior Art

Gamma detection cameras, also called gamma cameras, are used for medical imaging of particular body tissues, organs, or bone that may otherwise not be available for examination. In a typical medical camera of this sort, a special gamma ray emitting radiopharmaceutical is injected into the body and accumulates into the area of interest within the patient. The patient is then placed within the medical camera's imaging surface. As is well known, the radiopharmaceutical emits gamma rays which are then detected by the gamma camera as a series of photon emissions from a specialized crystal layer. Before the gamma rays reach the crystal they travel through a collimator layer which allows only those gamma rays which travel perpendicular to the collimator's orientation. A matrix of photomultiplier tubes is optically coupled to the crystal layer to receive the photon bursts, or scintillations, within the crystal layer and converts these photon bursts into electrical signals indicating a spatial coordinate of the gamma radiation. By using computers and other processing equipment to store and display the signals from the gamma camera, an image of the organ containing the radiopharmaceutical can be obtained and displayed for examination and diagnosis. When the gamma camera rotates around the patient and transverse images are reconstructed the system is called an emission computed tomography or ECT system. The surface of the gamma camera which receives the gamma rays from the patient is called the imaging surface. Since the collimator of the gamma camera is the first or outermost layer of the gamma camera, the collimator surface is commonly referred to as the imaging surface of the camera.

In practice, an object (patient) is placed horizontally into a central location while a gamma camera rotates (transaxial rotation) around a predetermined portion of the object to collect a number of images about that portion. This "ECT" rotation is orthogonal to the cranial-caudal axis of the patient. The acquired images are reconstructed into cross-sectional slices or images of the patient or object organ (or bone) at the predetermined location along the cranial-caudal axis of the object. For an total body scan, the gamma camera moves along the patient. As the camera surface translates, it collects the radiated gamma rays from the radiopharmaceutical. To obtain best quality images, it is desired to place the collimator surface as close as possible to the patient's outer surface. It is universally understood that when the collimator to patient distance is minimized better image resolution develops.

The resolution in the final reconstructed cross-sectional images is limited by the detector, the collimator, the distance between the collimator and the patient and by several other factors. One limitation is the sampling or size of the computer picture elements (pixels). Resolution improves if the size of the pixels is reduced (increased sampling). The gamma camera computer processor (image processor) processes a finite number of pixels to create an image. It would be advantageous to reduce the pixel size to improve image quality. The number of display pixels on the display screen, is distributed throughout the field of view of the imaging surface of a scanning camera. Therefore, a small object located within a large field of view of the imaging surface may appear relatively small on the display screen.

Recent ECT scanning cameras contain large rectangular field of views, typically 20 inches by 15 inches in dimension. This value represents the area of the imaging surface (collimator layer) of an ECT scanning camera. This is enough to accommodate the width of a human chest for a total body scan. However, if the particular organ or tissue of interest is only on the order of 4 to 5 inches wide, its representative image on the display screen will be small relative to the large field of view of the imaging surface. To this extent, relevant features of the small object may become obscured, hidden or difficult to interpret using a large field of view camera. To solve this problem, prior an systems have created a zoom region over a portion of the total field of view of the imaging surface. This zoom region has a zoom field of view that is smaller than the total field of view. The zoom region may be thought of as the active scanning region of the imaging surface; while those areas of the imaging surface not in the zoom region are passive in that they are temporarily not sending data to be imaged. For instance, for a square ECT imaging surface 20 inches by 15 inches, the zoom region may become 10 inches by 10 inches in area. The smaller zoom region (area) would then totally exist within the field of view of the imaging surface of the camera. All of the pixels available to the scanning camera would then be employed on this zoom region. The resulting image display of the small object within this zoom region would be larger than if the small object was imaged by the entire field of view.

The image discrimination resolution of a gamma camera is typically about 3–4 min. The resolution of the collimator is about 6 to 20 mm depending on the proximity of the collimator to the object. Given a 20 inch by 20 inch field of view there are approximately 508 mm by 508 mm in the field of view. Using an ECT study of 64 by 64 pixels, each pixel is approximately 9 mm by 9 mm in dimension. If the field of view of the imaging surface was reduced to 300 mm then the dimension of the pixel is now 5 mm and capable of finer discrimination of the object and the radiopharmaceutical. Typical resolution of the gamma camera is from 10–15 mm thus pixels are approximately 5–7.5 mm in dimension. Therefore, by reducing the field of view of the gamma camera, the resultant pixel dimension reduces in size and the imaging camera is capable of discerning more image detail. By utilizing the above procedure, a small object or organ can be displayed with excellent resolution by relatively minor modifications to an existing ECT system.

FIG. 1 illustrates the zoom region implemented in the prior art as discussed above. FIG. 1 is a frontal view along the long axis of the ECT scanning camera in one dimension. The side view of one position of the imaging surface 200 of an ECT camera is illustrated. A relatively small object 59 is also shown. In a well known manner, this ECT camera may rotate about a center of rotation 10 along a gantry structure (not shown) during the ECT scan; this rotation is called ECT movement. The object of interest 59 is located about the center of rotation 10 of the ECT system. The fixed location zoom region 80 of imaging surface 200 is also shown as the shaded portion. By locating the object of interest in and around the center of rotation 10, when the imaging surface rotates to a new position 200' (shown by the dashed lines), the zoom region 80 of the imaging surface remains in exactly the same relative fixed location with respect to the imaging surface. As is seen within position 200' the zoom region 80 is still located within the center of imaging surface 200'.

Systems of the prior art usually locate the object of interest close to the center of rotation of the ECT system because the zoom region 80 of the prior art systems occupies a fixed location with respect to the dimensions of the imaging surface 200. Therefore, as the imaging surface 200 moves through position 200', the zoom region 80 remains situated within the same relative position with respect to the imaging surface. However, if the object 59 was located off of the center of rotation 10, the object would not remain within the fixed zoom region 80 throughout the ECT scan movement because the imaging surface rotates around the center of rotation and not around the object. This is disadvantageous because in many ECT scanning operations it is desirable to place the object of interest as close to the imaging surface as possible to increase the quality of the resultant image. By placing the object 59 close to the imaging surface the object is inherently placed off of the center of rotation of the ECT camera.

Also, some scanning camera systems employ dual camera imaging surfaces that may be placed orthogonal to each other. It would be desirable to place the object 59 as close as possible to each imaging surface for high quality images. However, it is impossible to place the object 59 close to both orthogonal imaging surfaces while maintaining the object 59 within the center of rotation 10 of both imaging surface. It is desirable, rather, to place the object in the inside corner of the two imaging surfaces. Therefore, what is needed is a system capable of defining a zoom region corresponding to the initial placement of an object of interest within the field of view of an imaging surface then allow the relative position of that zoom region with respect to the imaging surface to move during ECT motion of the imaging surface. This would allow an object to be placed in the corner of two orthogonal imaging surfaces because the zoom regions (relative to the imaging surface) of each imaging surface could vary during the ECT motion of the imaging surface. The present invention allows for such an advantageous capability.

Therefore, it is an object of the present invention to allow a zoom region within an imaging surface of an ECT camera to be initially defined by the position of an object of interest (that may be off of the center of rotation of the imaging surface), then to move the zoom region relative to the imaging surface as the imaging surface undergoes ECT motion around the object of interest. In so performing the above, it is an object of the present invention to image a point of interest located on an object of interest where the point of interest is not located on the center of rotation of the ECT camera system. It is further an object of the present invention to advantageously utilize the above capability within the environment of a dual scanning camera ECT system. Therefore, the zoomed region will track a small point of interest or an organ of interest that is offset from the center of rotation of the ECT camera system. These and other objects of the present invention not specifically mentioned will be further discussed in the detailed discussion of the present invention.

RELATED PATENT APPLICATIONS

The following related co-pending application for patent having Ser. No. 07/981,833, and entitled, Proximity Detector for Body Contouring System of a Medical Camera, and assigned to the assignee of the present application for patent is herein incorporated by reference.

SUMMARY OF THE INVENTION

The present invention includes embodiments relating to apparatus operating in an imaging camera system having a gantry structure; a camera detector with an imaging surface; and a gantry control unit for rotating the imaging surface, the gantry control unit coupled to the gantry structure, a system for improving the resolution and relative size of a resultant image, the apparatus including: means for determining dimensions and initial location of a zoom region, the zoom region associated with a portion of the imaging surface; and means for displacing the zoom region relative to the imaging surface so that a field of view associated with the zoom region remains aligned with an object during relative displacement with respect to the object and the imaging surface, the means for moving the zoom region communicatively coupled to the means for determining the zoom region.

Embodiments of the present invention further include an apparatus as described above and wherein the relative displacement with respect to the object and the imaging surface occurs when the gantry control means rotates the imaging surface relative to the object during a scanning session of the camera scanning system and when a means for displacing the object displaces the object to minimize separation between the imaging surface and the object.

Embodiments of the present invention further include an apparatus as described above further including: data processing means for preprocessing image data gathered by the imaging surface at discrete rotation angles of the imaging surface during the scanning session, the data processing means coupled to the camera detector; and display processing means for processing for display only image data associated with the zoom region of the imaging surface, the display processing means coupled to the means for displacing the zoom region.

BRIEF DESCRIPTION OF THE DRAWINGS

FIG. 1 is an illustration of the prior art system illustrating zoom regions that are fixed in position with respect to associated imaging surfaces during ECT movement.

FIG. 2 illustrates both the ECT camera system of the present invention as well as the computer processing system of the present invention.

FIG. 3 is a block diagram illustrating elements of the computer processing system of the present invention.

FIG. 4 represents an illustration of a frontal view of the camera system of the present invention and an object advantageously placed off set from the center of rotation.

FIG. 5 is a flow diagram illustrating overall program flow executed by the computer processing system of the present invention.

FIG. 6A is a frontal view structural diagram of the camera system of the present invention illustrating the procedure used to determine the coordinate values of the point of interest.

FIG. 6B is a diagram of the preferred embodiment of the present invention illustrating the dimensions of the procedure used to calculate the coordinate values of the point of interest.

FIG. 6C is a diagram of an embodiment of the present invention illustrating the dimensions of the procedure used to calculate the coordinate values of the point of interest.

FIG. 7 is a frontal view structural diagram of the camera system of an alternative embodiment of the present invention illustrating the dimensions of the procedure used to determine zoom regions based on a displaced object.

FIG. 8A is a frontal view structural diagram of the camera system of the preferred embodiment of the present invention illustrating the dimensions of the procedure used to determine zoom regions based on a displaced object and rotating imaging surfaces.

FIG. 8B is a frontal view structural diagram of the camera system of an alternative embodiment of the present invention illustrating the dimensions of the procedure used to determine zoom regions based on a displaced object and rotating imaging surfaces.

DETAILED DESCRIPTION OF THE INVENTION

The preferred embodiment of the present invention includes a system allowing a zoomed region of an imaging surface of an ECT camera to automatically track a small object as the imaging surface undergoes ECT movement. In this way the small object may be advantageously placed off center from the center of rotation of the imaging surface while maintaining within the zoom region during ECT motion. In an effort to bring the object as close to the imaging surface or surfaces of the ECT camera system, it becomes necessary to displace the object from the center of rotation of the ECT scanning system. In the following detailed description of the present invention numerous specific details are set forth in order to provide a thorough understanding of the present invention. However, it will be obvious to one skilled in the art that the present invention may be practiced without these specific details. In other instances well known methods and apparatus have not been described in detail as not to unnecessarily obscure the present invention.

FIG. 2 illustrates an overall perspective view of a gantry structure and associated components for a medical camera of the present invention. The gantry structure 205 is a supporting structure which provides a mounting and alignment surface for elements of the present invention. The circular portion of gantry structure 205 provides support for multiple gamma camera detectors 200, and camera detector 210 and an optional counterweight 201. In one embodiment of the present invention, the surface of camera detector 200 is orthogonal to the imaging surface of camera detector 210, however multiple orientations between the camera imaging surfaces are within the scope of the present invention. Therefore, it is appreciated that the present invention is not limited to the environment of dual camera detectors located orthogonal to each other. However, this arrangement provides a convenient environment in which to discuss several aspects of the present invention. As will be further developed, the present invention may operate within a variety of different camera arrangements. The base of the gantry is located on tracks 250. A table 115 runs through the gantry structure 205 to provide support for a patient or for any object of interest; in the nuclear medicine field the object is typically a patient. Gantry structure 205 allows upper gamma camera detector 200, camera detector 210 and lower counterweight 201 to pivot circularly around the patient when the patient is located on table 115. The imaging surfaces of gamma camera 200, 210 are each a rectangular area approximately 15 inches by 20 inches wide while the outside dimensions are 22 inches by 27 inches. Movable table 115 is supported by a table actuator (base) 117.

The entire gantry structure 205 is capable of moving in the directions of tracks 250, under direction of a gantry track actuator, to cover the entire body of a patient reclined on table 115. A gantry control unit 252 moves the camera imaging surfaces 200, 210 in a circular direction around the gantry structure during an ECT scan operation. Since the gantry structure is capable of moving along track 250 a total body scan of a patient may be accomplished. The table 115 is also capable of moving the patient, if required. A three dimensional coordinate system (X, Y, Z) is shown for reference with the proximity determination system. The gantry structure 205 exists parallel to the XZ plane while the gantry system moves along the Y axis up or down track 250. Therefore, according to this coordinate system, each separate body image scanned by the imaging surfaces of cameras 200, 210 resides within the same XZ plane and is associated with a constant Y coordinate.

Referring still to FIG. 2, in the present mode, the gamma camera detectors 200, 210 are not capable of radial movement inward and outward, toward the patient and away from the patient when they are oriented orthogonal to each other. When the gamma camera detectors 200, 210 are moved in a circular motion around gantry 205 this is called ECT movement; the gantry control unit 252 is also capable of moving the imaging surfaces in the ECT direction. When the gantry structure moves along track 250, along the cranial-caudal axis of the reclined patient, this is called cranial-caudal axis movement of the gamma camera detector. Therefore, throughout this discussion reference will be made to cranial-caudal axis movement and ECT movement of the gamma camera detector of the present invention.

The imaging surfaces 200, 210 of the present invention are coupled to a computer processing system 270. Image data is fed to the computer processing system 270 from the camera imaging surfaces 200, 210. The gantry control unit 252 is also coupled to and controlled by the computer processing system 270. In this manner the computer processing unit 270 controls the ECT movement of the imaging surfaces 200, 210. In FIG. 2 the computer processing system 270 is shown with a user interface device 275 which includes a keyboard device and a screen positioning device (such a mouse device). A display screen 280 is included within the computer system 270 for displaying representative computer generated images of the data collected by imaging surfaces 200, 210. On the display screen 280 is shown a cross sectional view of a object 59. The computer processing system 270 also controls the gantry track actuator which controls the movement of gantry structure 205 along track 250. The computer processing system 270 also controls the position of table 115.

For each Y position of the gantry system along track 250, the camera units 200, 210 as shown in FIG. 2 provide image data of a particular slice of the patient to construct an image of the patient. Typically an image is made of several slices. However, the present invention operates on objects that are typically smaller than the imaging surface of the camera detectors. That is to say, the entire object of interest is much smaller than the field of view of each imaging surface. Therefore, movement along track 250 of the gantry to collect successive image slices of the present invention is usually not done in relation to the present invention. Rather, ECT motion is the crucial motion of the ECT scanning detectors 200, 210 of the present invention.

Generally, the computer processing system 270 used by the preferred embodiment of the present invention as illustrated in block diagram format in FIG. 3, comprises a bus 100 for communicating information, a central processor, 101 coupled with the bus for processing information and instructions, a random access memory 102 coupled with the bus 100 for storing information (image data and/or minimization determination data) and instructions for the central processor 101, a read only memory 103 coupled with the bus 100 for storing static information and instructions for the processor 101, a data storage device 104 such as a magnetic disk and disk drive coupled with the bus 100 for storing information and instructions, a display device 280 coupled to the bus 100 for displaying image and instruction information to the computer user, an alphanumeric input device 275 including alphanumeric and function keys coupled to the bus 100 for communicating information and command selections to the central processor 101, a cursor control device 107 coupled to the bus for communicating user input information and command selections to the central processor 101, and a signal generating device 108 coupled to the bus 100 for communicating command selections to and from the processor 101 to the ECT scanning camera, such as to control the gantry control unit 252, the gantry track actuator, and the position of table 115. Block 107, block 275 and block 280 comprise the user interface.

In the present invention the signal generation device 108 acts as a communication and control interface between the computer processing system 270 and the elements of the ECT scanning camera which are mounted about gantry 205. Interface unit 108 includes an analog to digital converter (and vice-versa) to transform analog position indication data from the ECT camera into digital form so that the computer processing system 270 can interpret data coming from the units of the ECT scanning camera. Unit 108 also includes a digital to analog converter to transform digital control data from the computer processing system 270 to analog form which is used to control the elements of the ECT scanning camera, such as gantry control unit 252, the gantry track actuator and the position of table 115. Specifically, the computer processing system utilized by the present invention includes a 29000 processor which is a special purpose data acquisition processor available by National Semiconductor and a SPARC workstation available from Sun Microsystems.

Referring still to FIG. 3, the display device 280 utilized with the computer processing system 270 and the present invention may be a liquid crystal device, cathode ray tube, or other display device suitable for creating graphic images and alphanumeric characters (and ideographic character sets) recognizable to the user. The cursor control device 107 allows the computer user to dynamically signal the two dimensional movement of a visible symbol (pointer) on a display screen of the display device 280. Many implementations of the cursor control device are known in the art including a trackball, mouse, joystick or special keys on the alphanumeric input device 275 capable of signaling movement of a given direction or manner of displacement. It is to be appreciated that the cursor means 107 also may be directed and/or activated via input from the keyboard using special keys and key sequence commands. Alternatively, the cursor may be directed and/or activated via input from a number of specially adapted cursor directing devices, including those uniquely developed for the disabled. In the discussions regarding cursor movement and/or activation within the preferred embodiment, it is to be assumed that the input cursor directing device or push button may consist any of those described above and specifically is not limited to the mouse cursor device.

Refer now to FIG. 4 which illustrates a frontal view of the ECT camera system illustrated in FIG. 2. FIG. 4 illustrates the preferred embodiment of the present invention utilizing one scanning camera surface in two positions, a first position 200 and a second position 200'. According to the advantageous technique of the present invention, the object 59 has been placed at a location offset from the center of rotation 10 in an effort to minimize the distance between the surface of object 59 and the imaging surface during the ECT scan where the imaging surface rotates about point 10. The collimator to object separation is minimized in order to improve the image quality of the resultant display. In the first position, zoom region 80 occupies the upper portion of the imaging surface. This zoom region is focused on the object 59 which is smaller than the total field of view of the entire imaging surface. In the second position, the area representing zoom region 80 has shifted in position along the imaging surface relative its initial position. In the second position the zoom region area 80 is on the right side of the imaging surface. For clarity, only the side view of zoom region 80 is illustrated in FIG. 4.

For every point along the are of the path that the imaging surface makes as it rotates from the first position 200 to the second position 200', the position of the zoom region 80 is modified to track the relative displacement of the object 59. The X and Z coordinates of the zoom area are altered but the Y coordinates of the zoom area remain constant. In this way the field of view determined by the zoom region remains aligned with the object 59 during ECT rotation. As is illustrated, the zoom region 80 shifted to the right hand position since object 59 moved relative to the imaging surface to the right side of the imaging surface position 200'. If this was not accomplished (i.e., the zoom region 80 was fixed at its initial position), the zoom region 80 at the second position would be on the left side out of the view of the object 59. It is clear that this position would be not be a desirable result because the object 59 would be out of the field of view of the zoom region. Therefore, the present invention includes a system which prevents the object 59 from moving outside the field of view of the zoom region due to mechanical motion of the imaging surface by moving the zoom region of the imaging surface in concert with the relative movement of the object 59.

The present invention offers a system for automatically adjusting a zoom region area across an imaging surface in order to track the relative displacement of the object 59 of interest. To this extent it is appreciated that either the imaging surface 200 can move around the object 59, or the object can move relative to the imaging surface 200, or a combination of both. Also, embodiments of the present invention disclose systems utilizing the type of zoom region described above in an environment having one imaging surface (one zoom region) or a multiple number of imaging surfaces (multiple zoom regions). The below discussions illustrate in detail the procedure and system components required to implement the automatic tracking system of the present invention. It is appreciated that automatic tracking is the ability to predict how a zoom region will track a small object (organ) of interest that is offset from the center of rotation of the ECT cameras during mechanical rotation of the imaging surface.

OVERALL FLOW OF THE PRESENT INVENTION

Refer to the logic block diagram flow of FIG. 5. FIG. 5 illustrates a high level flow diagram of the major processes (logic steps) of the present invention. At logic block 400 the present invention resets the ECT scanning system to prepare the system for an new ECT scan session. This includes initializing the computer processing system 270 for the scan session as well as moving the imaging surfaces 200, 210, the gantry structure 205 and the table 115 into their initial positions. Once the initialization is complete, at logic block 401 the object to be scanned is placed onto table 115 and positioned with respect to the imaging surfaces 200, 210 for the initial placement calibration. Block 401 may include moving the table 115 to position object 59 or moving the imaging surfaces 200, 210 or moving both. In any case, in block 401 the object is initially placed and aligned into the ECT scanning system. Next, at logic block 402 of the present invention the user sets the zoom region 80 for each imaging surface with respect to the desired object of interest 59 by inputting data to the user input device 275 into the computer processing system 270. Once the object 59 is initially oriented with respect to the imaging surfaces 200, 210, the user can display an image of the object 59 from the imaging surfaces onto the display screen 280. This initial image encompasses a field of view of an entire imaging surface.

Continuing processing under block 402, next the user selects the zoom dimensions of the zoom region. The dimensions of the desired zoom region area will correspond to the size of the organ or object of interest. The present invention will operate under a number of zoom regions having a number of dimension areas from zero to the complete field of view dimension of the imaging surface. For simplicity, one aspect of the present invention provides a number of discrete zoom region areas measured in one inch increments for each dimension. Each discrete zoom region area as an associated display box with representative dimensions. The user selects the appropriate box via user interface 275 that corresponds to the desired zoom region dimensions. Typical box sizes range from 10 inch square, 12 inch square and 15 inch square; however a variety of square or rectangular areas may be advantageously utilized in the present invention. Each box contains an "X" located in the mid section and may be moved around the display screen 280 by the user interface 275 or by the cursor control device 107. For each view associated with an imaging surface 200, 210, the user places the "X" mark over the center portion of the object 59 of interest using either the input device 275 or the cursor control device 107. This point of interest is called the POI of the object 59. The box will then completely outline the area and location of the desired zoom region which will automatically correspond to the area of interest of the object.

Referring to the flow of FIG. 5, it is appreciated that a zoom region box discussed above is placed for each imaging surface 200, 210. It is also appreciated that embodiments of the present invention using only one imaging surface input the positions of the required two boxes at different positions of the single imaging surface. That is to say, at a first position of the imaging surface the user inputs a first box location and then instructs the computer system to displace the imaging surface to another position where another box location is selected. Once the two boxes are placed, the user activates the computer processor system 270 to determine the coordinates of the POI 30 which task is accomplished by the processing of logic block 403. Using the placement of the two zoom regions on each imaging surface 200, 210, the computer processing system 270 of the present invention calculates the coordinates of the POI 30 and stores that data in the computer processing system memory. The POI is the center location of each box. It will be appreciated that the two selected zoom boxes may be of varying sizes thus offering more flexibility to the user in the display resolution of the object image. Using zoom boxes of different sizes, aspects of the same object 59 may appear on the display screen having different resolution. The details of the POI 30 location calculation will be further described in discussion to follow.

Next, at logic block 404 the present invention directs the computer processor system 270 to request the particular ECT scan parameters for the ECT scan session. This includes parameters associated with the angle of rotation for the imaging surfaces and the amount of angle displacement for each ECT scan in the session. The initial ECT scan position of the imaging surfaces can also be supplied at block 404 as well as information indicating if the current session is a pilot scan. Next, the present invention directs the processing to begin the ECT scan operation for a session at logic blocks 405–409. The computer processing system 270 controls the ECT movement of the imaging surfaces 200, 210 around gantry structure 205 by gantry control unit 252 at logic block 405. If necessary, the computer processing unit 270 can also adjust the position of the gantry structure 205 along the axial track 250.

At blocks 405 to 409, the computer processing system 270 performs a number of calculations and issues a number of control orders in real-time for the elements of the gantry structure, including the advantageous zoom tracking functions of the preferred embodiment of the present invention to perform an overall ECT scan session. During a typical ECT scanning session various movements of the elements on gantry structure 205 are possible. First, the imaging surfaces 200, 210 undergo a rotation or ECT motion around the object 59 placed on table 115; this occurs at block 405. At block 406, computer processing system 270 calculates the new position of the object to minimize the distance between the object and the imaging surface. Secondly, table 115 is adjusted by the computer processing system 270 in order to minimize the distance between the surface of the object 59 and the imaging surfaces of camera heads 200, 210; this also occurs at logic block 406. During block 407 locations are determined for new zoom regions reflecting the above displacements. The computer processing system 270 of the present invention must calculate new positions of the zoom regions with respect to the imaging surfaces for each movement of (1) the imaging surfaces around the object and (2) and for each movement of the object with respect to the imaging surfaces; this zoom location determination occurs at logic block 407.

At logic block 408, the computer processing system 270 directs the imaging surfaces 200, 210 to collect the image data for processing. Also accomplished by processing block 408, the preprocessed image data from the imaging surfaces are masked using the location of the zoom region so that only the preprocessed data from the imaging surfaces which are also associated with the zoom region of each imaging surface are processed by the resultant image developing routines of the computer processing system 270. Block 408 also processes this mask data for image display formats and stores the data for other retrieval functions. At logic block 409, the present invention directs the computer processing system 270 to determine if the ECT scan session is complete. If so, this portion of the processing ends at block 410 and the ECT scan session is complete. If the ECT scan session is not complete then another ECT angle of rotation is required for scan. The computer processing system is then directed to block 405 to process data associated with the next ECT angle of rotation until the ECT session is complete. At logic block 410 the resultant image captured by the zoom regions is displayed on display 280.

Referring to FIG. 5, under the processing of blocks 405–409, for each ECT angle position of the camera heads 200, 210 the computer system of the present invention simultaneously adjusts the positions of the imaging surfaces at block 405, calculates and adjusts the position of table 115 to minimize the collimator to patient separate at block 406, calculates new positions of each zoom region at processing block 407 and also collects the image data of the object 59 from each imaging surface at block 408. The session will continue for a new data collection at block 409; eventually the image is displayed at block 410. It is appreciated that a complete ECT scan session comprises several data collection steps occurring at individual and successive discrete ECT angle positions.

FIG. 6A and FIG. 6C illustrate the procedure by which the present invention determines the coordinates (X, Z) of the POI based on the center points of the two zoom regions selected by the user at block 402. The present invention determines these POI coordinates during the processing of block 403 as discussed above. This step is necessary in order to fix a coordinate position of the object 59 for use in other steps of the present invention.

FIG. 6A illustrates a frontal view of the present invention along the cranial-caudal axis (Y-axis) of the table 115. A side view of the imaging surfaces 200, 210 is shown. The locations of two predetermined and positioned zoom regions 80, 81 are shown in bold for clarity. Object 59 is illustrated with a point of interest POI 30 located offset from the center of rotation COR 10 of the imaging surfaces. The POI 30 is in both fields of view of the zoom regions 80, 81 by definition. In this view, imaging surface 200 is orthogonal to imaging surface 210 but may be at any orientation. Point 60 represents the center point along the side dimension of imaging surface 210 while point 62 represents the center point along the side dimension of imaging surface 200. The length o2 at reference 50 represents the distance between the center point of imaging surface 200 and the center of the zoom region 81 associated with this imaging surface. Also, length o1 at reference 52 represents the distance between the center of imaging surface 210 and the zoom region 80 associated with this imaging surface. It should be noted that the positions of the zoom regions of each imaging surface are displaced by adjusting the center position of each zoom region. The outer end boundaries of each zoom region are then determined with reference to the new center location and the total dimension of each zoom boundary, which is a constant value during an ECT scanning session.

PREFERRED EMBODIMENT

FIG. 6B illustrates a geometric diagram of the important relationships used in the POI 30 coordinate (X, Z) value determination step of the preferred embodiment of the present invention. DA1 is the angle of rotation with respect to imaging surface 210 and DA2 is the angle of rotation with respect to imaging surface 200. The values POIx and POIz are the values of the point of interest which are to be determined. The length o1 (52) is the known length between the center point of imaging surface 210 and the center of the zoom region 80 associated with imaging surface 210 while the length o2 (50) is the known length between the center point of imaging surface 200 and the center of the zoom region 81 associated with imaging surface 200. These lengths are known because the user input the location of each zoom region via the computer processing system. The processing of the preferred embodiment of the present invention at block 403 then determines the coordinates of the point of interest, POI(X, Z), according the below steps. The equation of lines o1 and o2 are expressed below.

$$z = \tan[DA1] * x + (o1 / \cos[DA1]) \text{ Line } o1$$
$$z = \tan[DA2] * x + (o2 / \cos[DA2]) \text{ Line } o2$$

Simultaneously solving for x and z yields the following equations:

$$K = \sin[DA2 - DA1]$$
$$POIx = (o1 * \cos[DA2] - o2 * \cos[DA1]) / K$$
$$POIz = (o1 * \sin[DA2] - o2 * \sin[DA1]) / K$$

Therefore, using the above relationships and steps, the processing of the preferred embodiment of the present invention of block 403 computes the (X, Z) coordinates of the point of interest POI 30. At block 402 the zoom region dimensions and positions are input by the user for zoom regions 80, 81. The centers of the zoom region positions will determine the values o1 and o2 for the above steps. The value, K, will be known before the ECT scan session by setting the orientation between the imaging surfaces 200 and 210 (usually 60, 90, or 120 degrees) and will remain constant during the ECT scan session. The angles of ECT rotation, DA1 and DA2, of the imaging surface 210 and 200 are also known quantities since the computer processing system 270 knows at all times the rotation angles of the imaging surfaces. At block 403, once the zoom regions 80, 81 are determined the preferred embodiment of the present invention then instructs the computer processing system to input the required values as described above and determine the values POIx and POIz. These coordinate values are then stored within the computer processing system 270 for later access.

It is appreciated that the above POI 30 coordinate position determination step may be accomplished via two imaging surfaces in different positions, each having an associated zoom region (as discussed above), or, alternatively the above step may be accomplished using only one imaging surface having an associated zoom region but positioned at two different orientations about the object 59. In either fashion, enough data will be gathered for the above steps to advantageously determine the coordinate value of POI 30.

ALTERNATIVE EMBODIMENT

FIG. 6C illustrates a geometric diagram of the relationships used in an alternative POI 30 coordinate (X, Z) value determination step of another embodiment of the present invention. The distance d1 referenced by 70 is the straight-line distance between the POI 30 and the center of rotation 10 at a given Y-axis position. Angle shown as a0 (78) represents the angle between the two imaging surfaces 200, 210 and remains constant throughout a scanning session. The angle a1 (72) represents the angle of rotation of the imaging surface 210 and is determined by the angle made by a line between the X-axis and the center point 60 of imaging surface 210. The angle a2 (74) must be determined based on these values given. The length o1 (52) is the known length between the center point of imaging surface 210 and the center of the zoom region 80 associated with imaging surface 210 while the length o2 (50) is the known length between the center point of imaging surface 200 and the center of the zoom region 81 associated with imaging surface 200. The processing of the present invention at block 403 then determines the coordinates of the point of interest, POI(X, Z), according the below steps.

$$d1 = sqrt[o1^2 + o2^2 - (2*o1*o2*cos(a0))]$$

Where "sqrt" is the square root function. When the two imaging surfaces 200, 210 are positioned orthogonal, the angle a0 becomes 90 degrees and the above step becomes simplified to:

$$d1 = sqrt[o1^2 + o2^2].$$

The angle a2 is then determined by the present invention by the following processing step:

$$a2 = \arccos\left[\frac{o2^2 + d1^2 - o1^2}{2 * o2 * d1}\right].$$

Finally, the (X, Z) coordinates of POI 30 can be determined by the steps of:

$$POIx = d1 * \sin[a1 + a2] \text{ and}$$

-continued
$$POIz = d1 * \cos[a1 + a2].$$

Expressing the above relationships (for 90 degree oriented imaging surfaces) in terms of the ECT angle position of the imaging surfaces (a1) yields the below step:

$$POIx = o2 * \sin[a1] + (o1 * \cos[a1]) \text{ and}$$
$$POIz = o2 * \cos[a1] - (o1 * \sin[a1]).$$

For the arrangement where the two-imaging surfaces are positioned either at 60 degrees or 120 degrees with respect to one another the present invention utilizes the below steps to compute the coordinate value of POI 30. As shown, variable, k, is determined by the angle formed between the imaging surfaces, a0.

$$k = 2 * o1 * o2 * \cos[a0]$$

$$POIx = \frac{\sin[a1]*(2*o2^2 - k) + \cos[a1]*sqrt[4*o2^2*o1^2 - k^2]}{(2 * o2)}$$

$$POIz = \frac{\cos[a1]*(2*o2^2 - k) - \sin[a1]*sqrt[4*o2^2*o1^2 - k^2]}{(2 * o2)}$$

Therefore, using the above relationships and steps, the processing of an embodiment of the present invention of block 403 computes the (X, Z) coordinates of the point of interest POI 30. At block 402 the zoom region dimensions and positions are input by the user for zoom regions 80, 81. The centers of the zoom region positions will determine the values o1 and o2 for the above steps. The value a0 will be known before the ECT scan session by setting the orientation between the imaging surfaces 200, 210 (usually 60, 90 or 120 degrees) and as discussed this value remains constant during the ECT scan session. The angle of ECT rotation, a1, of the imaging surface 210 is also a known quantity since the computer processing system 270 knows at all times this rotation angle. At block 403 once the zoom regions 80, 81 are determined the present invention then instructs the computer processing system to input the required values as described above and determine the values POIx and POIz. These coordinate values are then stored within the computer processing system 270 for later access.

ALTERNATIVE EMBODIMENT

FIG. 7 illustrates a diagram used by an alternative embodiment of the present invention to determine the position of the zoom regions 80, 81 when the position of the object 59 displaces relative to fixed imaging surfaces. This displacement typically occurs by direction of the minimization determination system (block 406) which offsets the object from the center of rotation 10 to minimize the distance between the object 59 and the imaging surfaces to increase image display quality of the camera system. Depending on the mode of operation of the ECT scan session (set in block 404), the zoom region determination procedures are executed during the processing of block 407. As noted above, during an ECT scan session, the imaging surfaces rotate through ECT motion and the table 115 also displaces in order to minimize the distance between the object 59 and the imaging surfaces 200, 210. The details of the minimization determination system are not crucial to the operative aspects of the present invention and therefore these details are not discussed at length herein as to not unnecessarily obscure the present invention. However, the minimization determination system is discussed in detail within the above referenced related patent application which is incorporated herein by reference. It is appreciated that the present invention at block 407 adjusts the position of the zoom regions 80, 81 in response to movements of the object 59 located on table 115 which is adjusted by the minimization determination system (also called the proximity determination system).

The following discussion illustrates the procedures of the present invention utilized to adjust for changes in the object position relative to the imaging surfaces. FIG. 7 is a frontal view of along the cranial-caudal axis (the Y-axis) of the ECT system of the present invention. FIG. 7 illustrates a object 59 having a POI 30 at two different locations, a first position represented by POI 30 and a second position represented by POI 30′. Zoom regions 80 and 81 on the imaging surfaces 210 and 200 respectively correspond to the first position of object 59 while zoom regions 80′ and 81′ on the imaging surfaces 210 and 200 correspond to the second position of the object 59. As table 115 moves object 59 from the first to the second position, processing block 407 calculates the new zoom regions 80′ and 81′ to track the motion of the object 59.

The goal of the below processing of this step of the present invention is to output two values, o1″ and o2′ which represent the change in location of the new zoom regions in response to the displacement of object 59 from the first to the second position. The values o1 and o2 represent the offset distance from the centers of imaging surfaces 200, 210 of zoom regions 80 and 81 respectively. By combining o1′ and o2′ with the old values o1 and o2, the positions of the new zoom regions are determined by the present invention during processing block 407. The new coordinate value of the object 59 in the second position is identified as POIx′ and POIz′. This value is known because the minimization determination system of the computer processing system 270 calculated this value and instructed table 115 to move the object 59 to this position. Therefore, the difference between the new object 59 position POI′ 30′ and the old object 59 position POI 30 is a known quantity. The distance, d1, between the first and second position of the object 59 and the value of a0 is determined by the present invention by the following processing steps.

$$d1 = \text{sqrt}[\ (POIx - POIx')^2 + (POIz - POIz')^2\ ]$$
$$a0 = \arcsin[\ (POIz - POIz') / d1\ ]$$

Referring still to FIG. 7, the angle made by a line from the center of imaging surface 200 to the center of rotation 10 is called the angle of imaging surface 200, or simply DA2. The value of angle a1 is therefore equal to the expression $(180 - DA2) - a0$. Further, the angle made by a line from the center of imaging surface 210 to the center of rotation 10 is called the angle of imaging surface 210, or simply DA1. Therefore, the angle a2 is equal to $DA1 + a0$. Lastly, the value of angle a3 is a known quantity and is either 60, 90, or 120 depending on the orientation of imaging surfaces 200, 210. Given the angles a1, a2, a3 and the value d1, the determination steps for o1′ and o2′ are given below for angle a3 equal to 120 or 90 degrees, which are the most common orientations.

$$o1' = (d1 * \sin[a2]) / \sin[a3]$$
$$o2' = (d1 * \sin[a1]) / \sin[a3]$$

A generic step utilized by the present invention for any given angle a3 is expressed below. The constant K equal the value of sin(a3): The value R1 equals POIx−POIx′ while R2 equal POIz−POIz′. Then the values o1′ and o2′ can be determined by the present invention according to the relationships:

$$o1' = (R1 * \sin[DA1] + R2 * \cos[DA1]) / K$$
$$o2' = (R1 * \sin[DA2] + R2 * \cos[DA2]) / K$$

The value o1′ represents the difference between the center of the zoom region 80 and the center of the new zoom region 80′ while the value o2′ represents the difference between the center of the zoom region 81 and the center of the new zoom region 81′. Since the value of angles a3, DA1, and DA2 associated with the orientation of the imaging surfaces 200, 210 are known, the values of o1′ and o2′ depend on the new variables POIx′ and POIz′; this result is anticipated since the new zoom regions 80′ and 81′ are calculated in response to the movement of object 59 from the first position POI to the second position POI′. Therefore, during an ECT scanning session whereby the object 59 is moved by the table 115 in relation to the imaging surfaces 200, 210, the computer processing system 270 at blocks 405–409 will perform the above functions to arrive at and thereby adjust the zoom regions on both imaging surfaces to track the movement of the object 59. By adjusting the locations of the zoom regions, the object 59 remains within the field of view of each zoom region and is thereby imaged by the ECT system with higher resolution as discussed previously.

PREFERRED EMBODIMENT

FIG. 8A illustrates the calculations performed by the preferred embodiment of the present invention in order to adjust the zoom regions of imaging surfaces 200, 210 when (1) the imaging surfaces move through ECT rotation along gantry 205 and when (2) the position of the object 59 also moves by direction of the minimization determination system. Depending on the mode of operation of the ECT scan session (set in block 404), these zoom region determination procedures are executed during the processing of block 407. This is the most commonly used determination procedure of the present invention since each ECT scan session involves both movements described above. During ECT movement, the imaging surfaces 200, 210 are rotated by gantry control unit around the center of rotation 10 at discrete angles. For each angle, scan data is gathered by each surface and reported to the computer processing unit 270.

The output of the processing block 407 for these determination steps will be the values o1′ and o2′ which now represent the displacements from the centers of imaging surfaces 210 and 200 respectively. Using these values, the new zoom regions 81 and 80 can be determined by the processing of the present invention. The processing required for this section occurs within block 407 of the overall flow which is accomplished by the computer processing system 270 of the present invention.

Refer to FIG. 8A illustrating the dimensions utilized in the procedure of the preferred embodiment of the present invention in order to determine the new zoom regions of imaging surfaces 200 and 210. The values POIx and POIz represents the new location of the object 30 as a result of ECT rotation of the imaging surfaces and/or displacement of the table 115. Angles DA1 and DA2 represent the rotation angles of imaging surfaces 210 and 200 respectively. The values of o1' and o2' represent the distances from the center of imaging surfaces 210 and 200 respectively to the new locations of zoom regions 80 and 81 respectively. The values of POIx and POIz are supplied from processing block 406. The value d is the distance of the POI 30 to the center of rotation 10. These values are computed according to the below processing steps:

$$d = \operatorname{sqrt}[\ (POIx)^2 + (POIz)^2\ ]$$
$$a1 = \operatorname{arcsin}[\ POIz\ /\ d\ ]$$
$$a2 = 180 - (a1 + DA1)$$
$$a3 = a1 - 180 + DA2$$

Lastly, the preferred embodiment of the present invention computes the values of o1' and o2' of FIG. 8A to determine the offset values of the center points 60, 62 of the zoom regions 80, 81 respectively by the processing steps shown below.

$$o1' = d * \sin[\ a2\ ]$$
$$o2' = d * \sin[\ a3\ ]$$

According to the above equations, the computer processing system 270 of the preferred embodiment, at block 407, computes new zoom regions 80 and 81 centered about points that are located at o1' and o2' distance offset from the centers 60, 62 respectively of imaging surfaces 210 and 200. From the center point of the zoom region, the location of the entire area of the zoom region with respect to the associated imaging surface is known. The movement of the point of interest POI 30 of object 59 is known by the computer processing system 270 at all time after the initial POI coordinate determination of block 403 is performed. Therefore, at all time during the ECT scanning session the coordinates of the POI 30 of the object 59 are known as the table 115 adjusts the object 59 position. Furthermore, the ECT angle or position of the imaging surfaces is known at all time during the ECT rotation of the imaging surfaces 200, 210. The angles DA1 and DA2 are known during a scanning session of the present invention. Using these basic relationships the above steps can be expressed as purely a function of the known values to determine the location along the imaging surfaces 210, 200 of the zoom regions 80, 81. These steps are presented below reduced to primary variables yields:

$$o1' = -(\ POIz * \cos[\ DA1\ ]) + POIx * \sin[\ DA1\ ])$$
$$o2' = -(\ POIz * \cos[\ DA2\ ]) + POIx * \sin[\ DA2\ ])$$

Given the above relationships, the computer processing system 270 at processing block 407 determines a location of the area of a zoom region at any POI 30' location given any set of ECT rotation angles of the imaging surfaces. In this way, the fields of view associated with each of the zoom regions 80, 81 can track the relative motion of the object 59 with respect to the imaging surfaces 200, 210. In this fashion the zoom regions will gather image data for a resultant display image of only the object of interest within a reduced field of view.

ALTERNATIVE EMBODIMENT

Refer to FIG. 8B which illustrates the dimensions used in the processing steps of an alternative embodiment of the present invention in order to adjust the zoom regions of imaging surfaces 200, 210 when (1) the imaging surfaces move through ECT rotation along gantry 205 and when (2) the position of the object 59 also moves by direction of the minimization determination system. As shown, the value DA1 is the angle between a line from the center 60 of imaging surface 210 to the COR 10 and the X-axis while the value DA2 is the angle between a line from the center 62 of imaging surface 200 to the COR 10 and the X-axis. The value of angle a1 is therefore equal to 180−DA2 while the value of angle a2 is equal to simply DA1. The value of r is the distance from the center of rotation 10 to the centers 60, 62 of imaging surfaces 200, 210; by definition the distances are equal. The distance d2 is the length from POI 30 to center 62. The distance d3 is the length between POI 30 and point 60. The distance d1 is the length between POI 30 and the COR 10. After the displacements of the imaging surfaces and the object, as discussed above, the processing of the present invention first calculates the positions of the centers 60, 62 of imaging surfaces 210, 200. This is accomplished through the below steps.

$$x62 = r*\sin[90 - a1] = r*\cos[a1] = -r*\cos[DA2]$$
$$z62 = r*\cos[90 - a1] = r*\sin[a1] = -r*\sin[DA2]$$
$$x60 = r*\sin[90 - a2] = r*\cos[DA1]$$
$$z60 = r*\cos[90 - a2] = r*\sin[DA1]$$

The center 60 of imaging surface 210 is represented by coordinate pair (60x, 60z) while the center 62 of imaging surface 200 is represented by coordinate pair (62x, 62z). Angle DA1 and DA2 are known because the computer processing system 270 adjusted these angles during the controlled ECT rotation about COR 10.

Referring still the diagram of FIG. 8B, the computer processing system 270 of an alternative embodiment of the present invention determines the values d1, d2, and d3 according to the below relationships.

$$d1 = \operatorname{sqrt}[\ (POIx)^2 + (POIz)^2\ ]$$
$$d2 = \operatorname{sqrt}[\ (POIx - 62x)^2 + (POIz - 62z)^2\ ]$$
$$d3 = \operatorname{sqrt}[\ (POIx - 60x)^2 + (POIz - 60z)^2\ ]$$

With these distances calculated, the present invention then determines the values of angles a3 and a4 of FIG. 8B by the below steps.

$$a3 = \operatorname{arccos}\left[\frac{d2^2 + r^2 - d1^2}{2*d2*r}\right]$$

$$a4 = \operatorname{arccos}\left[\frac{d3^2 + r^2 - d1^2}{2*d3*r}\right]$$

Lastly, the present invention computes the values of o1' and o2' of FIG. 8B to determine the offset values of the center points 60, 62 of the zoom regions 80, 81 respectively by the processing steps shown below.

$$o1' = d3 * \cos[90 - a4] = d3 * \sin[a4]$$
$$o2' = d2 * \cos[90 - a3] = d2 * \sin[a3]$$

The above may be expressed in terms of primary values as:

$$o1' = \text{sqrt}[\ x^2 * \sin^2[\partial] + z^2 * \cos^2[\partial] - 2*x*z*\sin[\partial]*\cos[\partial]\ ]$$
$$o2' = \text{sqrt}[\ x^2 + z^2 + \cos(2*\beta)*(z^2 - x^2) + (2*x*z*\sin[2*\beta])\ ]$$

Where: $x = POIx$ and $\partial = DA1$
$z = POIz$ $\beta = DA2$

Given the above relationships, the computer processing system 270 at processing block 407 determines a location of the area of a zoom region at any POI 30 location given any set of ECT rotation angles of the imaging surfaces. In this way, the fields of view associated with each of the zoom regions 80, 81 can track the relative motion of the object 59 with respect to the imaging surfaces 200, 210. In this fashion the zoom regions will gather image data for a resultant display image of only the object of interest within a reduced field of view.

PREFERRED EMBODIMENT

The preferred embodiment of the present invention employs two derivative processes in order to calculate the respective positions of new zoom regions based on: (1) a moving point of interest and fixed imaging surfaces; and (2) a rotating gantry and a fixed point of interest.

The adjustment processes of the preferred embodiment with respect to table movement in non-circular ECT studies is discussed first. Note that the table 115 will move in both X and Z directions. The process will require the relative change in X and Z positions from the original POI 30 to a new POI called POI' (see FIG. 7). The process is executed to calculate the zoom region adjustment for every new movement of the table 115. The values calculated by the derivative, $\Delta o1'$ and $\Delta o2'$ represent the offset or adjustment from the current zoom regions defined by o1 and o2 (see FIG. 6A). The process steps shown in detail are below.

$Rx = POIx - POIx'$ Change in x position
$Rz = POIz - POIz'$ Change in z position $\Delta o1' = -(Rx * \sin[DA1] + Rz * \cos[DA1])$
$\Delta o2' = -(Rx * \sin[DA2] + Rz * \cos[DA2])$ The processing of block 407 of the preferred embodiment of the present invention will perform the above procedure to arrive at the new zoom region positions along imaging surfaces 200 and 210 in response to a table 115 movement. Block 406 will provide the values Rx and Rz in the above procedure.

The adjustment processes of the preferred embodiment of the present invention with respect to gantry movement in noncircular and circular ECT studies is discussed. This process will determine the location of the new zoom regions in response to rotating imaging surfaces and a stationary table 115. The values DA1 and DA2 are the prior angles for imaging surfaces 210 and 200 respectively. The values DA1' and DA2' are the new angles for the new position of the imaging surfaces 210 and 200 respectively. Therefore, the processing computes the value of $\Delta o1'$ and $\Delta o2'$ by the following.

$\Delta o1' = POIz*(-\cos[DA1'] + \cos[DA1]) +$
$POIx*(-\sin[DA1'] + \sin[DA1])$ $\Delta o2' = POIz*(-\cos[DA2'] + \cos[DA2]) +$
$POIx*(-\sin[DA2'] + \sin[DA2])$ The values of DA1' and DA2' are supplied from processing block 405 of the present invention. The values above are determined in block 407 in order to determine the position of new zoom regions along the imaging surfaces 200 and 210.

EFFECT OF THE ZOOM REGIONS 80, 81

The image display capability of the computer processing system 270 is not infinite. The display device 280 contains a finite number of pixels, or picture elements, which can be used to generate a computer graphics image of object 59 and the ECT scanning camera system has a finite number of data points it may use to generate an image. The scanning camera heads 200, 210 of the present invention operate at a basic level under the technology of Anger type ECT cameras. Anger scanning cameras are well known in the industry and are used to detect radiated gamma rays originating from an object; each camera head contains a collimator layer on the imaging surface to collect and direct certain radiated gamma rays, a crystal layer to detect the incident gamma rays and create photo emissions, and a photomultiplier layer optically coupled to the crystal layer to detect the photo emissions and generate therefrom analog voltage signals which are preprocessed (using multiple correction factors) and used to indicate the position and intensity of the photo emissions. The scanning camera system of the present invention is able to detect images with a resolution of 4096 pixels by 4096 pixels. However, computer processing systems are not able to process and display an image with such great number of total pixels (i.e. $4096^2$) in real-time. The smallest pixel area size is determinable based on the area of the scanning surface and the pixels available therein.

For an imaging surface having a field of view of approximately 20 inches, the display resolution of the image is determined based on the number of pixels available to generate a display image on screen 280 spread across the entire field of view. In this case each pixel of an image represents an elemental area of the object that is relatively large. For instance, during the ECT mode of the scanning camera the computer processing system may gather a maximum of $128^2$ pixels arranged in a matrix of 128 pixels by 128 pixels as the imaging surfaces are rectangular. Therefore, the dimensions of each pixel are roughly on the order of 0.16 inches by 0.16 inches. The pixel imaging data collected for a 20 inch field of view generates an image of object 59 of all elements within the large field of view. Therefore, a four inch object of interest, say a heart, would have a relatively smaller display size with respect to the rest of object 59. In this size view, details of the heart could be obscured or completely hidden given this resolution allocation spread across the entire imaging surface.

On the other hand, a zoom region smaller than the 20 inch field of view of the imaging surface may utilize all of the data processing resolution available by the computer processing system 270 over a smaller area. Therefore, the full resolution capability of the overall ECT scanning system can be used to image the object of interest within the zoom region with greater resolution.

The resultant pixels represent a relatively smaller elemental area of the object imaged; thus image resolution of that object is increased and the overall image is displayed larger on the display screen 280 to illustrate more detail. For instance, a zoom region having an area of 10 inches by 10 inches will utilize the 128 by 128 pixel matrix; this yields a pixel size of 0.08 by 0.08 inches which is four times smaller in area than the pixels associated with the 20 inch field of view. This yields much better resolution for the object of interest as well as makes the object larger in the display screen 280.

The signals input from the photomultiplier tubes are analog voltage data. These signals are first preprocessed using multiple corrector factors (linearity, uniformity, and sensitivity) to generate an output which indicates the location (coordinate values) and intensity of photo emissions within the crystal layer across the entire surface of an imaging surface; for convenience this output is called the preprocessed photomultiplier output. It is preprocessed in that correction factors are applied before the data is imaged for display through the zoom regions. A zoom region is located on a portion of the imaging surface area and corresponds to a portion of the detector locations within that surface. The locations (coordinates) of the zoom region are identical to the coordinates that are reported by the preprocessed photomultiplier data. Therefore, when a zoom region is active, only the data reported by the preprocessed photomultiplier output that have matching coordinate locations within the zoom region are processed by the computer processing system 270 for image display purposes. Data from the preprocessed photomultiplier output having coordinates outside the zoom region are temporarily ignored by the image display functions of the computer processing system 270. Therefore, within the computer processing system a zoom region may also be viewed as a mask region because data within the preprocessed photomultiplier output falling outside the zoom region are masked out by the present invention while data falling inside the zoom region are masked in by the present invention. These masking operations of the preprocessed photomultiplier output database of the present invention are accomplished at processing block 408.

More specifically, a zoom region is an area location of a set of coordinate values centered at a POI 30 having fixed dimensions which are selected by a user; the set of coordinate values represents a area region of the associated imaging surface. Within the present invention the zoom region is square, however it is appreciated that any rectangular area may be used and will not depart from the scope of the present invention. The placement of a zoom region is therefore determined based on the location of the center of the zoom region. Once the center is known the boundaries of the zoom region are determined based on the fixed width across the associated imaging surface.

During a single ECT scan session, the present invention moves a zoom region by altering the center point of the zoom region and then determining a new set of coordinate values based on the new center and the fixed dimensions of the zoom region. Once the zoom region has moved a new mask is simultaneously generated. In the preferred embodiment of the present invention, the aspects of the above discussion are actually performed twice as there are two imaging surfaces and therefore multiple zoom regions. Therefore, each time a zoom region is altered by either a change in the POI 30 location or a change in the ECT angle of rotation of the imaging surfaces, or both, image data is collected from different areas of the imaging surfaces 200, 210 in an effort to track the relative movement of the object 59.

The above discussions regarding the procedure of the present invention to determine the new location of the zoom region illustrate that these new zoom locations are determined based on an offset from the center of the imaging surface. It should be noted that as the imaging surfaces undergo ECT rotation, the location of the zoom regions change in only one coordinate with respect to the two dimensional surface area. That is, the side view dimension illustrated in FIGS. 6, 7, and 8 of the imaging surfaces is the only dimension which is updated during zoom region displacement. The other dimension of the imaging surfaces, that is the dimension orthogonal to the diagrams, is not updated at all because there is not relative movement of the object and imaging surface with regard to this dimension during ECT rotation. According to the coordinate system employed by the present invention, the center of each zoom region will displace through the XZ plane, however will remain constant with respect to the Y axis. Therefore, to determine the exact location of the coordinate values of a zoom area within the imaging surface, the present invention determines the location of the zoom region center by: (1) determining the offset along a dimension in the XZ plane from the scanning center and then (2) determining the constant location in the Y axis. Finally the present invention locates the entire area of the zoom region by the fixed length and width of the zoom region about the determined zoom area center point.

The computer processing system 270 of the present invention performs the tasks of determining the locations of the zoom regions 80, 81 on each imaging surface 210, 200 based on the current orientation of the ECT imaging surfaces and the location of table 115. The computer processing system 270 next performs the masking function to read only image data from the ECT scanning camera that corresponds to the zoom regions. The computer processing system 270 also stores and generates an image on display 280 of the selected point of interest of object 59 based on the collected data. The computer processing system also controls the location of the imaging surfaces during the ECT movement as well as controls the location of table 115. The computer processing system 270 of the present invention also controls the gantry track actuator.

The preferred embodiment of the present invention, system for automatically displacing zoom regions on imaging surfaces of an ECT scanning camera so that the zoom regions track relative movement of an object during an ECT scan session to improve the resolution of the object is thus described. While the present invention has been described in one particular embodiment, it should be appreciated that the present invention should not be construed as limited by such embodiment, but rather construed according to the below claims.

What is claimed is:

1. An apparatus for increasing image resolution of an object in a nuclear imaging camera system comprising:
   an imaging surface for collecting image information, said imaging surface rotated through a plurality of angles about said object;
   a gantry coupled to said imaging surface for rotating said imaging surface about said object during a scanning operation;

first logic determining a zoom region associated with a portion of said imaging surface, said zoom region having an associated zoomed field of view aligning with said object; and wherein said first logic also automatically determines an updated position of said zoom region with respect to said imaging surface so that said associated zoomed field of view of said zoom region remains aligned with said object in response to said imaging surface rotating about said object.

2. An apparatus for increasing image resolution of an object in a nuclear imaging camera system as described in claim 1 wherein said first logic automatically determines an updated position of said zoom region for a given angle of said plurality of angles of said imaging surface according to a function of said given angle.

3. An apparatus for increasing image resolution of an object in a nuclear imaging camera system as described in claim 2 further comprising imaging logic for collecting image information from said imaging surface based on said updated position of said zoom region for individual angles of said plurality of angles.

4. An apparatus for increasing image resolution of an object in a nuclear imaging camera system as described in claim 2 wherein said imaging surface collects image information associated with said zoom region over said plurality of angles and further comprising display logic for generating an image for display based on said image information.

5. An apparatus for increasing image resolution of an object in a nuclear imaging camera system as described in claim 4 further comprising a user interface providing definition of dimensions of said zoom region and also providing definition of an initial location of said zoom region with respect to said imaging surface.

6. An apparatus for increasing image resolution of an object in a nuclear imaging camera system as described in claim 5 further comprising:

zoom region computation logic responsive to said user interface and defining a first location of a first zoom region with respect to said imaging surface at a first angle of said imaging surface;

wherein said zoom region computation logic also defines second location of a second zoom region with respect to said imaging surface at a second angle of said imaging surface; and coordinate computation logic determining a coordinate position of said object based on said first location, said second location, said first angle and said second angle.

7. An apparatus for increasing image resolution of an object in a nuclear imaging camera system as described in claim 5 wherein said user interface comprises:

a display unit displaying an full image of said object, said full image representative of a field of view for substantially all of said imaging surface;

a user input device positioning an indicator area over portions of said full image and providing selection of a particular portion of said full image; and zoom region computation logic determining said initial location of said zoom region with respect to said imaging surface by determining a region of said imaging surface having a field of view encompassing said particular portion of said full image selected by said user input means.

8. An apparatus for increasing image resolution of an object in a nuclear imaging camera system as described in claim 1 further comprising an object position device for providing a coordinate position of said object and wherein said first logic automatically determines an updated position of said zoom region for a given angle of said plurality of angles of said imaging surface according to a function of: (1) said given angle; and (2) said coordinate position of said object.

9. An apparatus for increasing image resolution of an object in a nuclear imaging camera system as described in claim 8 wherein said object may be offset from a center of rotation of said imaging surface.

10. A nuclear imaging system comprising:

a camera detector coupled to a gantry structure, said camera detector having an associated imaging surface;

a gantry control unit for rotating said imaging surface through rotation angles about an object, said gantry control unit coupled to control portions of said gantry structure;

first logic for determining dimensions and an initial location of a zoom region having an associated zoomed field of view aligned with said object, said zoom region associated with a portion of said imaging surface; and zoom region position computation logic for automatically determining updated positions of said zoom region relative to said imaging surface so that said zoomed field of view associated with said zoom region remains aligned with said object in response to said imaging surface rotating through said rotation angles, wherein said object may be offset from a center of rotation of said imaging surface.

11. A nuclear imaging system as described in claim 10 wherein said zoom region position computation logic automatically determines an updated position of said zoom region for a given angle of said rotation angles of said imaging surface according to a function of said given angle.

12. A nuclear imaging system as described in claim 11 further comprising:

data processing computer logic for preprocessing, in real-time, image data gathered by said imaging surface at individual rotation angles of said imaging surface, said data processing computer logic communicatively coupled to said imaging surface; and display processing logic for processing in real-time only that image data associated with said zoom region of said imaging surface; and a display device for displaying a zoomed image composed of said image data associated with said zoom region of said imaging surface, said display device communicatively coupled to receive information from said display processing logic.

13. A nuclear imaging system as described in claim 11 wherein said first logic for determining dimensions and initial location of a zoom region comprises:

second logic for displaying a full image of said object, said full image representative of a field of view for substantially all of said imaging surface;

a user interface for positioning an indicator area over portions of said full image and for selecting a particular portion of said full image; and third logic for determining said location of said zoom region with respect to said imaging surface by determining a region of said imaging surface having a field of view encompassing said particular portion of said full image selected by said user interface.

14. A nuclear imaging system as described in claim 11 further comprising object position calculation logic for determining a coordinate position of said object based on a location of a first zoom region and a location of a second zoom region, said first zoom region associated with a first rotation angle of said imaging surface and said second zoom region associated with a second rotation angle of said imaging surface.

15. A nuclear imaging system as described in claim 10 further comprising an object position device for providing a coordinate position of said object and wherein said zoom region position computation logic automatically determines an updated position of said zoom region for a given angle of said rotation angles of said imaging sur/ace according to a function of: (1) said given angle; and (2) said coordinate position of said object.

16. A nuclear imaging system as described in claim 15 wherein said object position device includes a movable table for displacing said object.

17. An apparatus for scanning an object by a nuclear imaging camera, said apparatus comprising:
a first imaging surface and a second imaging surface each positionable with respect to another at a predetermined angle;
a gantry structure for rotating said first imaging surface and said second imaging surface through a plurality of rotation angles about said object;
first logic for determining an initial position and dimension of a first zoom region of said first imaging surface and for determining an initial position and dimension of a second zoom region of said second imaging surface; and
zoom region computation logic for automatically determining updated positions for said first and said second zoom regions with respect to said first and said second imaging surfaces, respectively, so that zoomed fields of view associated with said first and said second zoom regions remain individually aligned with said object for each angle of said plurality of rotation angles of said first and said second imaging surfaces about said object.

18. An apparatus for scanning an object as described in claim 17 wherein said object may be positioned outside a center of rotation of said first and said second imaging surfaces.

19. An apparatus for scanning an object as described in claim 18 further comprising an object position device for providing a coordinate position of said object and wherein said zoom region computation logic automatically determines updated positions of said first and said second zoom regions for a given angle of said plurality of rotation angles according to a function of: (1) said given angle; and (2) said coordinate position of said object.

20. An apparatus for scanning an object as described in claim 19 further comprising:
image generation logic for generating an image of said object based on image information supplied from said first and said second zoom regions over said plurality of rotation angles; and
a display for displaying said image of said object.

21. An apparatus for scanning an object as described in claim 17 wherein said zoom region computation logic automatically determines updated positions of said first and said second zoom regions for a given angle of said plurality of rotation angles according to a function of said given angle.

22. An apparatus for scanning an object as described in claim 21 further comprising object position determination logic for determining a coordinate position of said object based on positions of said first zoom region and said second zoom region.

23. In a nuclear camera imaging system having an imaging surface and a gantry for rotating said imaging surface about an object, a computer implemented method for scanning said object, said computer implemented method comprising the steps of:
determining dimensions and initial location of a zoom region, said zoom region associated with a portion of said imaging surface;
rotating said imaging surface through a plurality of rotation angles about said object;
automatically determining updated positions of said zoom region relative to said imaging surface so that a field of view associated with said zoom region remains aligned with said object as said imaging surface rotates about said object.

24. A method of scanning an object as described claim 23 wherein the step of rotating said imaging surface comprises the step of positioning said object offset from a center of rotation of said imaging surface.

25. A method of scanning an object as described claim 24 further comprising the step of providing a coordinate position of said object and wherein said step of automatically determining updated positions of said zoom region comprises the step of automatically determining an updated position of said zoom region for a given angle of said plurality of rotation angles of said imaging surface according to a function of: (1) said given angle; and (2) said coordinate position of said object.

26. A method of scanning an object as described claim 23 wherein said step of automatically determining updated positions of said zoom region comprises the step of automatically determining an updated position of said zoom region for a given angle of said plurality of rotation angles of said imaging surface according to a function of said given angle.

27. A method of scanning an object as described claim 26 further comprising the steps of:
generating a zoomed image of said object according to image data of said object associated with said zoom region of said imaging surface for said plurality of said rotation angles; and
displaying said zoomed image on a display device.

28. A method of scanning an object as described claim 24 further comprising the step of determining a coordinate position of said object based on locations of a first zoom region and a second zoom region, said first zoom region associated with a first rotation angle of said imaging surface and said second zoom region associated with a second rotation angle of said imaging surface.

29. A method of scanning an object as described in claim 24 wherein said step of determining dimensions and initial location of a zoom region comprises the steps of:
displaying a full image of said object, said full image representative of a field of view for substantially all of said imaging surface;
with a user interface, positioning an indicator area over portions of said full image and selecting a particular portion of said full image; and
determining said location of said zoom region with respect to said imaging surface by determining a region of said imaging surface having a field of view encompassing said particular portion of said full image selected by said user interface.

* * * * *